United States Patent [19]
Shimono et al.

[11] Patent Number: 5,904,901
[45] Date of Patent: May 18, 1999

[54] DEODORIZATION/ODOR-REMOVAL/ DISINFECTION METHOD AND DEODORIZATION/ODOR-REMOVAL/ DISINFECTION APPARATUS

[75] Inventors: Kikuo Shimono; Eiichi Tominaga; Masao Kajimaki, all of Suita, Japan

[73] Assignee: Duskin Co., Ltd., Osaka, Japan

[21] Appl. No.: 08/913,773

[22] PCT Filed: Jan. 20, 1997

[86] PCT No.: PCT/JP97/00099

§ 371 Date: Sep. 22, 1997

§ 102(e) Date: Sep. 22, 1997

[87] PCT Pub. No.: WO97/26925

PCT Pub. Date: Jul. 31, 1997

[30]  Foreign Application Priority Data

Jan. 22, 1996  [JP]  Japan ................................... 8-008331

[51] Int. Cl.[6] ..................................................... A62B 7/08
[52] U.S. Cl. ......................... 422/120; 422/122; 422/123; 422/124; 422/186.07
[58] Field of Search .................................. 422/5, 29, 30, 422/186.07, 120, 123, 124, 122

[56]  References Cited

U.S. PATENT DOCUMENTS 4,550,010  10/1985  Chelu ........................................... 422/4
4,680,163   7/1987  Blidschun et al. ......................... 422/28
5,135,714   8/1992  Wang ......................................... 422/23
5,256,379  10/1993  DeLoach .............................. 422/186.3
5,259,962  11/1993  Later ....................................... 210/758
5,656,246   8/1997  Patapoff et al. ......................... 422/187

FOREIGN PATENT DOCUMENTS 4-15059   1/1992  Japan .
4-144672  5/1992  Japan .
4-166207  6/1992  Japan .
6-7420    1/1994  Japan .
9-60931   3/1997  Japan .

*Primary Examiner*—Krisanne Thornton
*Attorney, Agent, or Firm*—Evenson, McKeown, Edwards & Lenahan P.L.L.C.

[57]  ABSTRACT

A purpose of this invention is to provide an apparatus which can carry out a deodorization/odor-removal/disinfection work even on a large-scaled matter such as a room etc. effectively and efficiently. A deodorization/odor-removal/ disinfection apparatus of this invention is equipped with an ozone generator (1), an ozone blow-off mechanism which blows generated ozone from a blow-off port (12), a device (2) which atomizes aqueous hydrogen peroxide, and an aqueous hydrogen peroxide blow-off mechanism which blows the atomized aqueous hydrogen peroxide from a blow-off port (32). This apparatus generates ozone and at the same time produces aqueous hydrogen peroxide under atomized state, makes the both contact each other and then makes them contact with an object.

3 Claims, 4 Drawing Sheets

CONCENTRATION OF AQUEOUS
HYDROGEN PEROXIDE (W/V%)

DEODORIZATION/ODOR-REMOVAL/ DISINFECTION METHOD AND DEODORIZATION/ODOR-REMOVAL/ DISINFECTION APPARATUS

TECHNICAL FIELD

This invention relates to a method and an apparatus carrying out deodorization, odor-removal and disinfection by using ozone.

BACKGROUND ART

Deodorization and odor-removal by using ozone are frequently utilized. Free-hydroxyradical produced by reaction between ozone and water molecule decomposes various odorous substances, especially malodorous substances such as ammonia and isovaleric acid etc. to provide deodorization and odor-removal effects. The free-hydroxyradical is produced by methods (1) ozonolysis caused by ultraviolet radiation, (2) hydrogen peroxide decomposition caused by ultraviolet radiation, (3) ozonolysis caused by hydrogen peroxide catalyst etc., and is produced efficiently by the method (3) in particular.

Incidentally, the above-mentioned method (3) has so far been carried out by putting a matter to be treated into aqueous hydrogen peroxide and making ozone bubble in the aqueous hydrogen peroxide. In this method, however, it has been unable to deodorize and remove odor from a large-scaled matter, and an efficiency has been bad.

DISCLOSURE OF THE INVENTION

A purpose of this invention is to provide a method and an apparatus which can carry out a deodorization/odor-removal work and further a disinfection work even on a large-scaled matter such as a room etc. effectively and efficiently.

A first invention of this application is characterized by that, in a method carrying out a deodorization/odor-removal/disinfection work on an object, ozone is produced and at the same time aqueous hydrogen peroxide is produced in an atomized state, the both are made contact each other and then made contact with the object.

According to the above-mentioned first invention, a density of the ozone contacting with the aqueous hydrogen peroxide under atomized state becomes large, and a reaction between the ozone and water content is enhanced owing to catalyst action of hydrogen peroxide, so that the free-hydroxyradical can be formed efficiently. Consequently, a deodorization/odor-removal/disinfection effect can be improved. Further, since the ozone and aqueous hydrogen peroxide under atomized state contact each other while being dispersed, they reach widely every nook and corner to form the free-hydroxyradical. Therefore, the deodorization/odor-removal/disinfection work can be carried out over a wide range every nook and corner. In addition, since the required reaction is only to produce the ozone and the aqueous hydrogen peroxide under atomized state simultaneously, its workability is good.

In addition to the above first invention, the following constructions may be used.
(1) In the vicinity of the object, the ozone and the aqueous hydrogen peroxide under atomized state are made contact. According to this method, the deodorization/odor-removal/disinfection work can be carried out only on a desired spot in a concentrated manner. Further, since the ozone and the aqueous hydrogen peroxide can be utilized for the deodorization/odor-removal/disinfection work only on a desired spot so as to eliminate wasteful consumption of them, an increase in a raw material cost can be controlled. Moreover, since the free-hydroxyradical can be provided just in front of the desired spot, the deodorization/odor-removal/disinfection effect can be improved.
(2) After completion of the deodorization/odor-removal/disinfection work, residual ozone is recovered and decomposed. According to this method, the residual ozone at a site where the deodorization/odor-removal/disinfection work is carried out can be decomposed in an early stage and an entrance to the site can be accomplished in an early stage.

A second invention of this application is characterized by that, in an apparatus carrying out a deodorization/odor-removal/disinfection work of an object, there are equipped an ozone generator, an ozone blow-off mechanism which blows generated ozone from a blow-off port, a device which atomizes aqueous hydrogen peroxide, and an aqueous hydrogen peroxide blow-off mechanism which blows the atomized aqueous hydrogen peroxide from a blow-off port.

According to the above second invention, the method of the foregoing first invention can be realized by a simple construction.

In addition to the above second invention, the following constructions may be used.
(3) Both the ozone blow-off mechanism and the aqueous hydrogen peroxide blow-off mechanism have blow-off nozzles which can set the blow-off ports at any voluntary spots. According to this construction, the above method (1) can be realized by a simple construction.
(4) An ozone recovery and decomposition device is provided. According to this construction, the above method (2) can be realized by a simple construction.

BEST MODE FOR CARRYING OUT THE INVENTION

Figure 1:
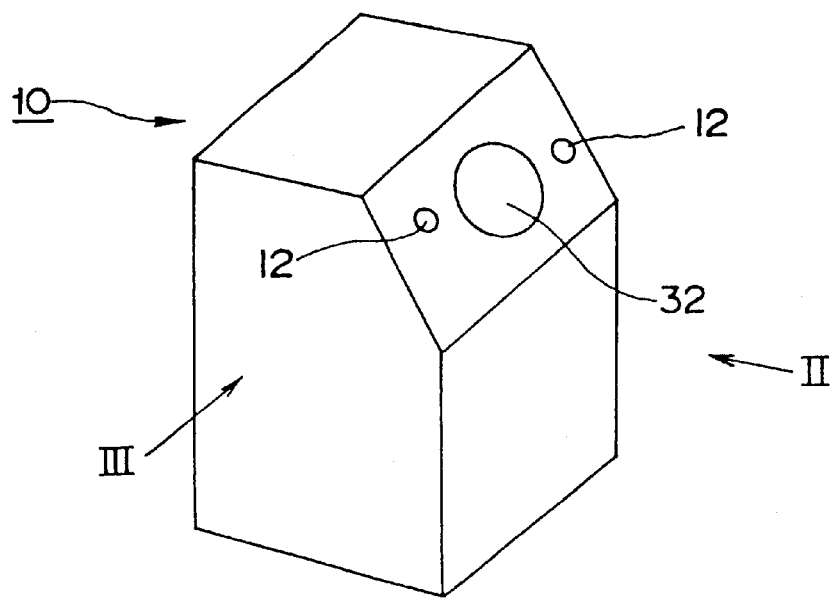
FIG. 1 is an oblique view of the deodorization/odor-removal/disinfection apparatus of this invention.
Figure 2:
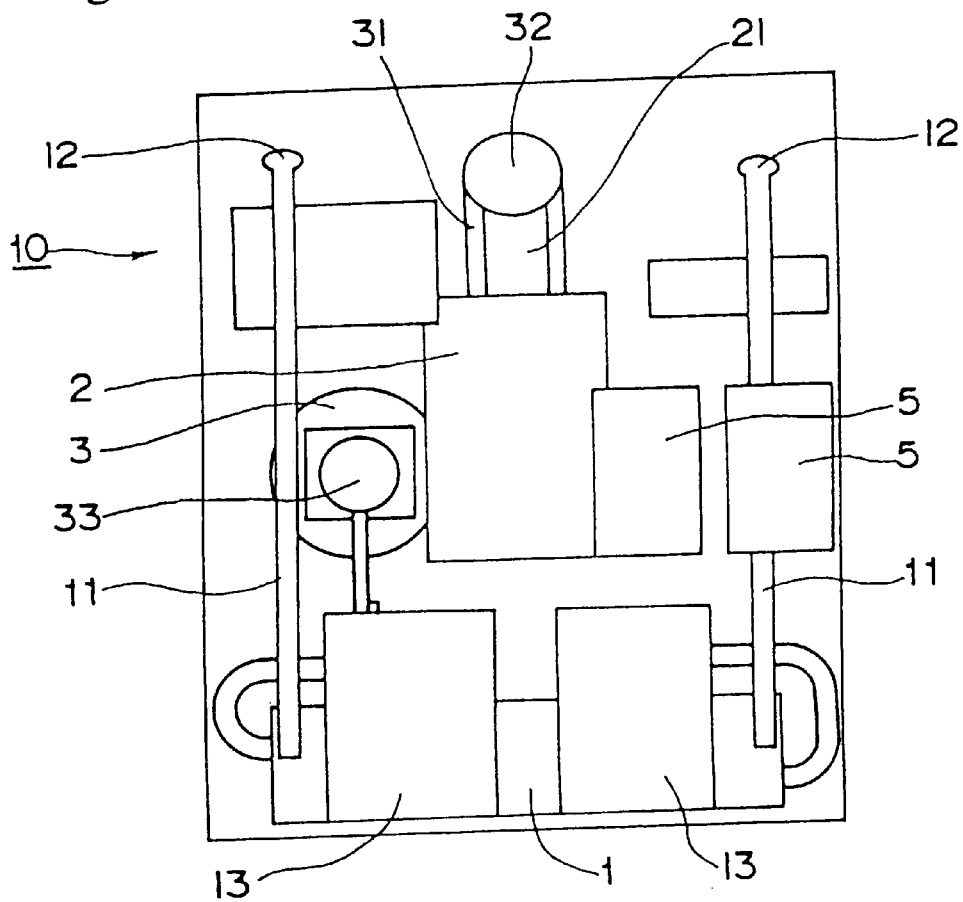
FIG. 2 is a perspective view viewed in a direction of arrow II of FIG. 1.
Figure 3:
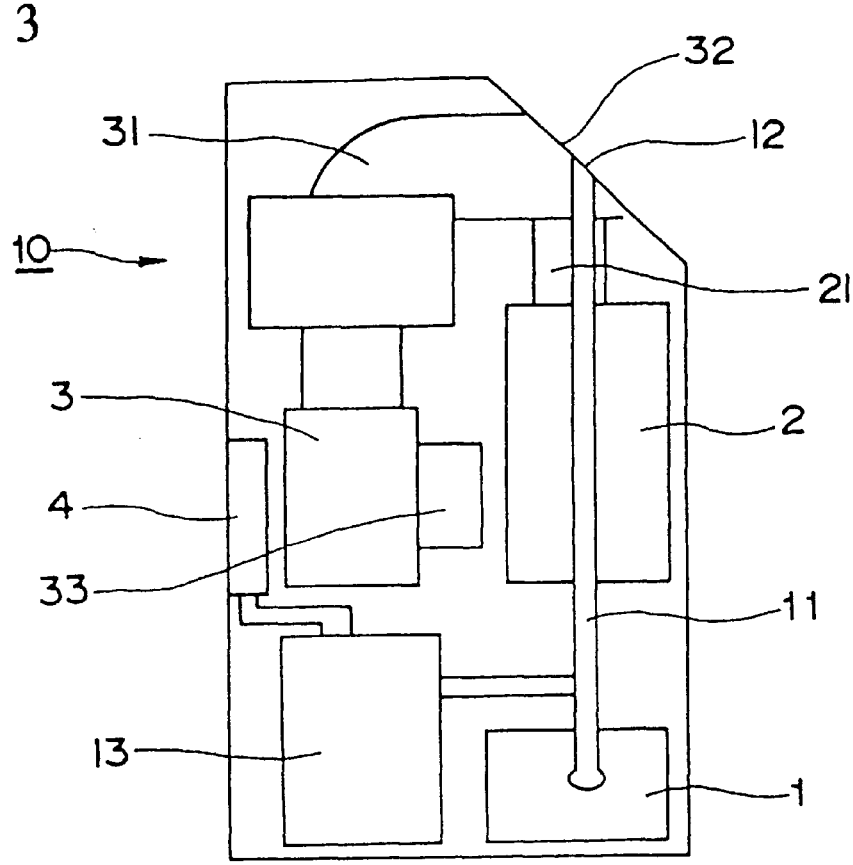
FIG. 3 is a perspective view viewed in a direction of arrow III of FIG. 1.

FIG. 1 is the oblique view of a deodorization/odor-removal/disinfection apparatus 10 of this invention. FIG. 2 is the perspective view viewed in a direction of arrow II of FIG. 1. FIG. 3 is the perspective view viewed in a direction of arrow III of FIG. 1. 1 is an ozone generator, 2 is an ultrasonic type atomization device which produces atomized aqueous hydrogen peroxide, 3 is a blower, 4 is an ozone recovery and decomposition device, and 5 is a power supply.

Passages 11 for passing the generated ozone extend to an upper part from both sides of the ozone generator 1, and the passages 11 open to atmosphere at blow-off port 12. The ozone generated in the ozone generator 1 is designed to be blown off by a pump controller 13 from the blow-off port 12 through the passages 11. Thereby, an ozone blow-off mechanism is composed.

A ventilation passage 31 extending from the blower 3 opens to atmosphere at a blow-off port 32. 33 is a motor for the blower 3. A passage 21 for passing atomized aqueous hydrogen peroxide extends to an upper part from the atomization device 2, and the passage 21 opens in the vicinity of the blow-off port 32 of the ventilation passage 31. Thereby, an aqueous hydrogen peroxide blow-off mechanism is composed. The atomization device 2 atomizes the aqueous hydrogen peroxide down to a particle diameter able to reach the object without being settled, and preferably to a diameter ranging from 10 to $0.5\mu$. For the atomization device 2, not only the ultrasonic type but [1] a spray gun type, [2] a venturi tube type, or a type in which liquid is supplied to a tube intersecting at right angle with a direction of high-speed air flow so as to be atomized, and [3] a type in which supersaturated gas is atomized by using a condensation nucleus, may be used.

The ozone recovery and decomposition device 4 includes an ozone decomposition agent, and is so controlled by a pump controller 13 as to suck ozone blown off to atmosphere when a fixed time has elapsed, after completion of generation of ozone in the ozone generator 1.

In the deodorization/odor-removal/disinfection apparatus 10 having the foregoing construction, the ozone generated in the ozone generator 1 is blown off from the blow-off port 12 through the passage 11 to atmosphere. At the same time, the aqueous hydrogen peroxide atomized by the atomization device 2 is blown off through the passage 21 to the ventilation passage 31, and blown off by the blower 3 to atmosphere from the blow-off port 32. The blown off ozone and aqueous hydrogen peroxide under atomized state contact each other while being dispersed to atmosphere.

By the way, ozone reacts with water content to produce free-hydroxyradical. This production reaction is enhanced by catalyst action of hydrogen peroxide. Therefore, when the ozone contacts with the aqueous hydrogen peroxide under atomized state, the free-hydroxyradical is produced efficiently. In addition, the aqueous hydrogen peroxide is under the atomized state so that a density of ozone contacting with it becomes large. From this point again, the free-hydroxyradical is produced efficiently. The free-hydroxyradical offers an odorous substance decomposition function and a bactericidal function.

Figure 4:
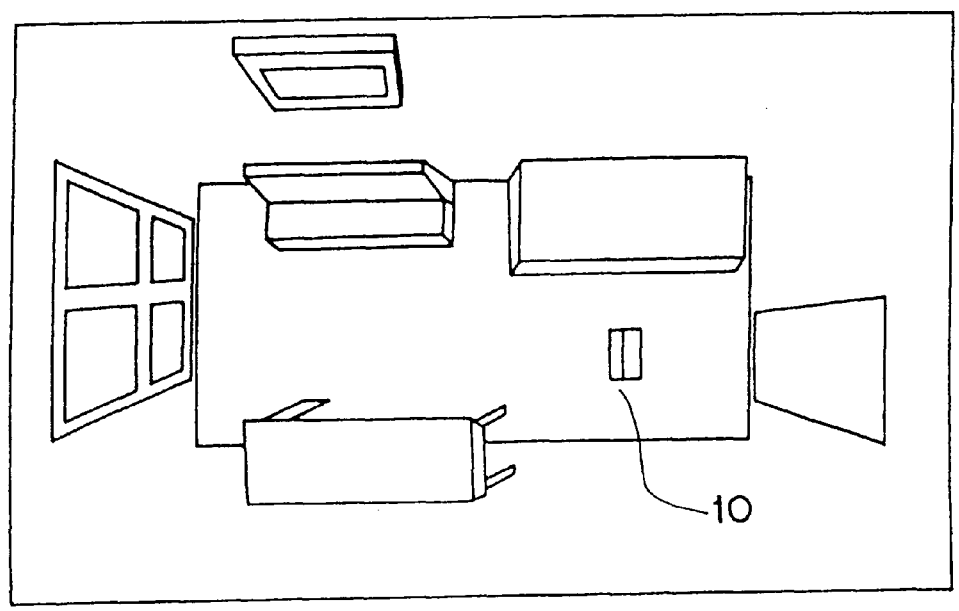
FIG. 4 is a plan view showing a state where the deodorization/odor-removal/disinfection apparatus of FIG. 1 is used for a room.

Accordingly, the deodorization/odor-removal/disinfection apparatus 10 having the above-mentioned construction can produce the free-hydroxyradical so that it can exert the deodorization/odor-removal/disinfection effect. In addition, it can produce the free-hydroxyradical efficiently so that it can exert an excellent deodorization/odor-removal/disinfection effect. For example, as illustrated by FIG. 4 showing the plan view of one room, when the deodorization/odor-removal/disinfection apparatus 10 having the foregoing construction is installed in the room to have it operate, the ozone and the aqueous hydrogen peroxide under atomized state are generated simultaneously from the separate blow-off ports 12 & 32, and contact each other while being dispersed so as to produce the free-hydroxyradical efficiently. Since the ozone and the aqueous hydrogen peroxide under atomized state disperse in the room every nook and corner, the free-hydroxyradical is produced at any place in the room and odorous substances are decomposed in every places in the room and bacterium are destroyed. Namely, the room is deodorized, removed odor and disinfected.

When a fixed time i.e. a time required for the deodorization/odor-removal/disinfection work has elapsed after completion of generation of the ozone and aqueous hydrogen peroxide under atomized state, the ozone recovery and decomposition device 4 operates. The ozone recovery and decomposition device 4 sucks ozone remaining in the room and decomposes it by an ozone decomposition agent. Entrance in the room is impossible while the ozone is remaining because it has toxicity. However, the ozone is removed by the ozone recovery and decomposition device 4 within a short time, so that entrance in the room becomes possible in an early time.

Figure 5:
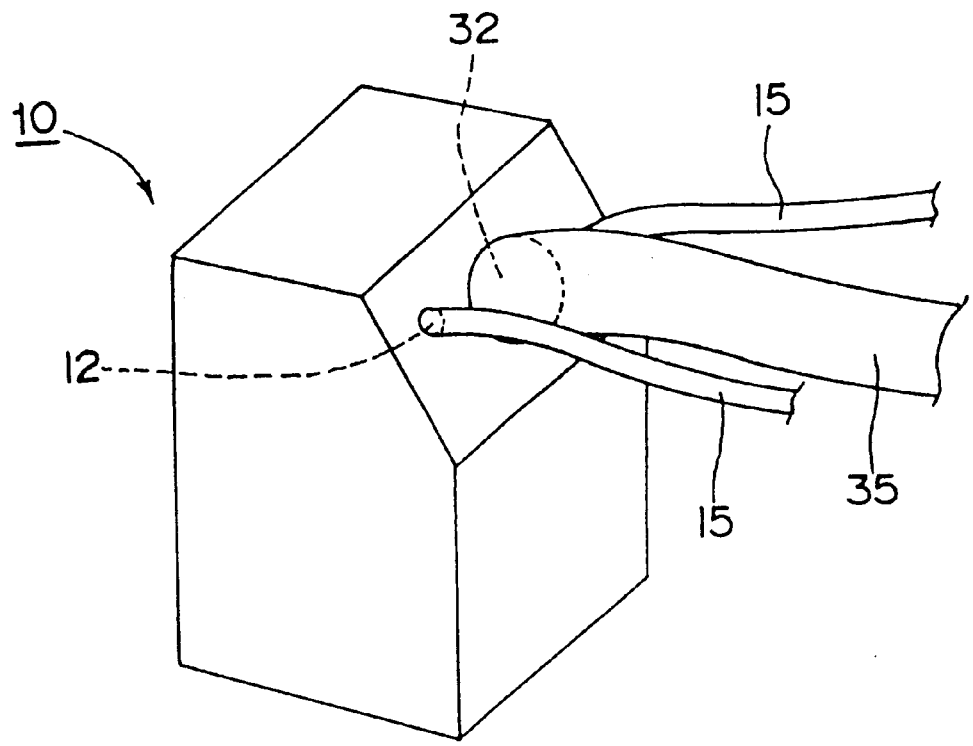
FIG. 5 is an oblique view of the deodorization/odor-removal/disinfection apparatus to which nozzles are attached.
Figure 6:
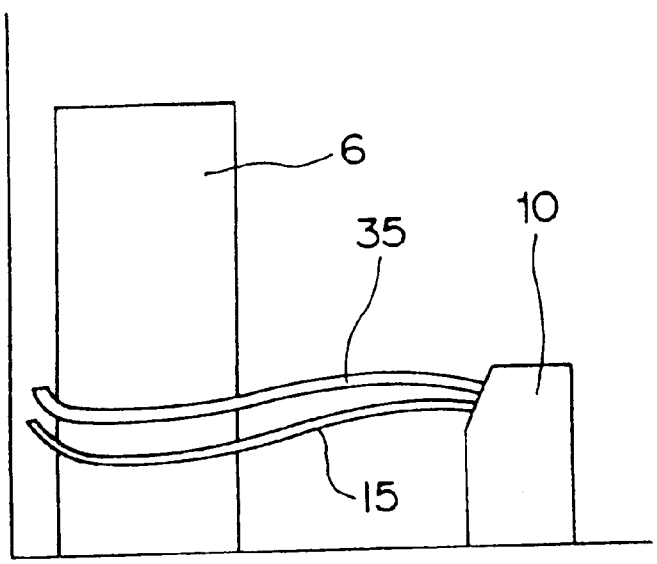
FIG. 6 is a side view showing one mode of utilization of the deodorization/odor-removal/disinfection apparatus of FIG. 5.

FIG. 5 is the oblique view showing a state where the nozzles 15 & 35 are attached to the blow-off ports 12 & 32 of the deodorization/odor-removal/disinfection apparatus 10 having the foregoing construction. The nozzles 15 & 35 are made of hose-like long materials opening at their tip ends. The deodorization/odor-removal/disinfection apparatus 10 having the foregoing construction attached with the nozzles 15 & 35 are used as shown by FIG. 6, for example. Namely, the tip ends of the nozzles 15 & 35 are located at a spot such as a backside of chest of drawers 6 to be subjected to the deodorization/odor-removal/disinfection work, ozone is blown off from the nozzles 15 at that spot, and at the same time aqueous hydrogen peroxide under atomized state is blown off from the nozzle 35 so as to make the both contact each other.

According to this method, the deodorization/odor-removal/disinfection work is done only on a desired spot such as a backside of the chest of drawers 6 concentrically. Further, since the ozone and aqueous hydrogen peroxide are used only for the deodorization/odor-removal/disinfection work of the subject spot, they are not consumed wastefully and consumption efficiency is improved. In addition, since the ozone and aqueous hydrogen peroxide under atomized state contact each other just in front of the subject spot to produce the free-hydroxyradical, the free-hydroxyradical is also utilized effectively and the deodorization/odor-removal/disinfection effect is improved.

As mentioned above, the deodorization/odor-removal/disinfection apparatus 10 having the foregoing construction is designed to produce the ozone and at the same time produces the aqueous hydrogen peroxide under atomized state, and make the both contact each other to produce the free-hydroxyradical. Thereby, odorous substances are decomposed and bacterium are destroyed. Further, the nozzles 15 & 35 are attached to the apparatus, so that the ozone and aqueous hydrogen peroxide under atomized state are made contact each other in the vicinity of the object to produce the free-hydroxyradical. Moreover, the residual ozone is recovered and decomposed by the ozone recovery and decomposition device 4 after completion of the deodorization/odor-removal/disinfection work.

Figure 7:
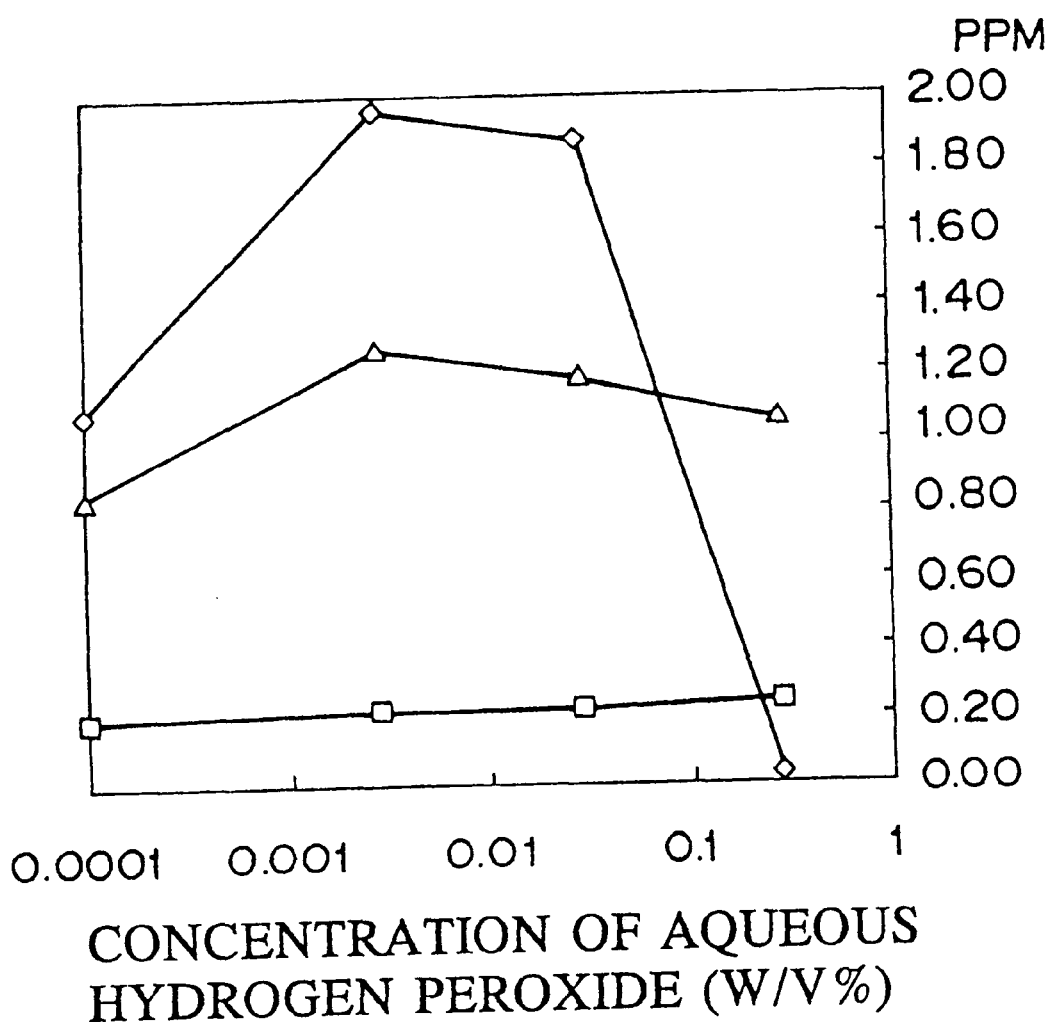
FIG. 7 is a graph showing investigation results of optimum concentration of aqueous hydrogen peroxide.

FIG. 7 shows experimental results for investigating the optimum concentration of aqueous hydrogen peroxide put in use. In the figure, the axis of abscissa represents a concentration of aqueous hydrogen peroxide (w/v %) and the axis of ordinate represents an ozone decomposition quantity (ppm). Marks □ indicate a case where the ozone generation quantity is 0.6 ppm, marks Δ indicate a case where the ozone generation quantity is 3.8 ppm, and marks ◊ indicate a case where the ozone generation quantity is 14 ppm. Respective spots represent 0.0001 w/v %, 0.0028 w/v %, 0.028 w/v %, and 0.28 w/v %.

As seen from FIG. 7, the ozone decomposition quantity scarcely relates to the concentration of aqueous hydrogen peroxide in case where the ozone generation quantity is small, but the concentration of aqueous hydrogen peroxide gives a large influence on the ozone decomposition quantity as the ozone generation quantity increases. This tendency can be understood from the fact that, as the ozone generation quantity increases, a shape of graph becomes convex to upper. It can be said that the concentration of aqueous hydrogen peroxide optimum for decomposition of ozone lies roughly within a range from 0.001 to 0.1 w/v %.

EMBODIMENT (1) Deodorization/odor-removal effect (Test example)

A test relating to deodorization/odor-removal was carried out by using the deodorization/odor-removal/disinfection apparatus 10 having the foregoing construction. Test conditions were as follows:

[1] Two panels to which malodorous substances adhered were installed in a room having a specified area. Size of panel was 15 cm by 15 cm. Respective 2 ml of tobacco malodor, raw garbage malodor, and grease trap malodor were applied on the panels as malodorous source, and then dried.

[2] In the foregoing room, the apparatus 10 was operated under the following conditions.

Concentration of aqueous hydrogen peroxide: 0.028%, Density of ozone: 1.5 ppm

Spray quantity of aqueous hydrogen peroxide: 17 g/min., Ozone generation quantity: 400 mg/hr Operation time: 30 min., 60 min., 90 min.

[3] Fluctuation of odor was evaluated by four subjects according to their organoleptics.

(Comparison Test Example)

Comparison test was done only using the ozone generator without using the aqueous hydrogen peroxide, by three subjects. Another conditions were same with those of the test example.

(Results)

In the test example, when the operation time of 60 min. has elapsed, all the four subjects evaluated that the tobacco malodor was eliminated completely. However, two subjects evaluated that the grease trap malodor still remained and three subjects evaluated that the raw garbage malodor still remained. When the operation time of 120 min. has elapsed, two subjects who evaluated the remaining grease trap malodor recognized that the malodor decreased, and three subjects who evaluated the remaining raw garbage malodor recognized that the malodor decreased.

In the comparison test, when the operation time of 60 min. has elapsed, only one subject recognized a decrease in the tobacco malodor. Even the operation time of 120 min. has elapsed, all the three subjects evaluated that there was no difference from the operation time of 60 min.

From the above-mentioned fact, it can be seen that the deodorization/odor-removal effect is improved by the deodorization/odor-removal/disinfection apparatus 10 having the foregoing construction.

(2) Disinfection effect (Test example)

A test relating to disinfection was carried out by using the deodorization/odor-removal/disinfection apparatus 10 having the foregoing construction. Test conditions were as follows:

[1].A P-tile 30 cm long and 30 cm wide was placed in a room having a specified area. House dust of 0.1 g taken out of a vacuum cleaner was scattered on the tile.

[2] The apparatus 10 was operated in the above room under two conditions A and B.

Condition A: An oxygen bomb was connected to the ozone generator to generate ozone of high density. The maximum density of ozone was 29 ppm. A time after the density of ozone exceeded 10 ppm was measured as a processing time. The concentration of aqueous hydrogen peroxide was set to 0.03%.

Condition B: The ozone was generated without connecting the oxygen bomb. The density of ozone was stabilized in a range between 1.5 to 1.7 ppm. The concentration of aqueous hydrogen peroxide was set to 0.03%.

Operation time: 30 min., 60 min., 120 min.

[3] When operation of the apparatus 10 was completed, the house dust was recovered from the P-tile surface using a sterilized booth tampon, bacterium were extracted by a stomacher using LP diluted solution of 50 ml. Using this diluted solution as a sample solution, a number of bacteria in sample solution of 1 ml was investigated.

(Comparison test example)

Comparison test example 1: Comparison test was done only using the ozone generator to which the oxygen bomb was connected, without using the aqueous hydrogen peroxide, so that ozone of high density was generated. The maximum ozone density was 26 ppm. Another conditions were same with those of the test example.

Comparison test example 2: Water through which ozone was passed was used as ozone water, and this ozone water was sprayed in place of generating the ozone. The density of ozone lay within a range of 1.7 to 1.9 ppm. The aqueous hydrogen peroxide was not used. Another conditions were same with those of the test example.

(Results)

Results as listed in Table 1 were obtained. The disinfection effect could be recognized in the test example, but it could not be recognized in the comparison test examples 1 and 2.

TABLE 1

| Contents of test | Operation time | Number of general bacteria | Number of mold |
| --- | --- | --- | --- |
| Test example; Condition A: (High-density ozone + spray of aqueous hydrogen peroxide) | 30 min. 60 min. 120 min. | $2.85 \times 10^3$ $1.17 \times 10^3$ $1.68 \times 10^3$ | $6.50 \times 10$ $4.25 \times 10$ $4.75 \times 10$ |
| Test example; Condition B: (Low-density ozone + spray of aqueous hydrogen peroxide) | 30 min. 60 min. 120 min. | $9.35 \times 10^3$ $4.23 \times 10^3$ $4.52 \times 10^3$ | $6.35 \times 10$ $7.55 \times 10$ $5.55 \times 10$ |
| Comparison test example 1: (High-density ozone only) | 30 min. 60 min. 120 min. | $2.05 \times 10^4$ $2.20 \times 10^4$ $1.56 \times 10^4$ | $9.75 \times 10$ $1.07 \times 10^2$ $6.75 \times 10$ |
| Comparison test example 2: (Spray of ozone water only) | 30 min. 60 min. 120 min. | $1.83 \times 10^4$ $1.80 \times 10^4$ $1.64 \times 10^4$ | $1.03 \times 10^2$ $8.75 \times 10$ $8.75 \times 10$ |
| Not-processed | | $2.68 \times 10^4$ | $9.67 \times 10$ |

We claim:

1. An apparatus for deodorization and disinfection that is installed in and utilized for a room, comprising:

an ozone generator;

an ozone blow-off mechanism that blows generated ozone from blow-off ports into the room;

a device for atomizing aqueous hydrogen peroxide having a concentration of 0.001 to 0.1 w/v %; and an aqueous hydrogen peroxide blow-off mechanism for blowing atomized aqueous hydrogen peroxide from a blow-off port into the room.

2. The apparatus according to claim 1, wherein the ozone blow-off mechanism and the aqueous hydrogen peroxide blow-off mechanism comprise blow-off nozzles that can be set at a desired spot.

3. An apparatus according to claim 1, further comprising an ozone recovery and decomposition device.

* * * * *